United States Patent
Meester (10) Patent No.: US 11,925,327 B2
(45) Date of Patent: Mar. 12, 2024

(54) ENDOSCOPE COMPRISING A DICHROIC PRISM ASSEMBLY WITH AT LEAST FOUR CHANNELS

(71) Applicant: Quest Photonic Devices B.V., Wieringerwerf (NL)

(72) Inventor: Richard Johannes Cornelis Meester, Wieringerwerf (NL)

(73) Assignee: Quest Photonic Devices B.V., Wieringerwerf (NL)

(*) Notice: Subject to any disclaimer, the term of this patent is extended or adjusted under 35 U.S.C. 154(b) by 87 days.

(21) Appl. No.: 17/325,331

(22) Filed: May 20, 2021

(65) Prior Publication Data

US 2021/0267444 A1 Sep. 2, 2021

Related U.S. Application Data

(62) Division of application No. 16/082,550, filed as application No. PCT/NL2017/050825 on Dec. 8, 2017, now Pat. No. 11,064,874.

(30) Foreign Application Priority Data

Dec. 9, 2016 (NL) ...................................... 2017973

(51) Int. Cl.
*A61B 1/05* (2006.01)
*A61B 1/00* (2006.01)
(Continued)

(52) U.S. Cl.
CPC .......... *A61B 1/051* (2013.01); *A61B 1/00096* (2013.01); *G02B 23/2453* (2013.01);
(Continued)

(58) Field of Classification Search
CPC ................ A61B 1/051; A61B 1/00096; G02B 23/2453; G02B 23/2484; G02B 27/1013; G02B 27/141
See application file for complete search history.

(56) References Cited

U.S. PATENT DOCUMENTS 6,181,414 B1  1/2001 Raz et al.
6,330,113 B1* 12/2001 Slagle ................ G02B 27/1073
                                                        348/338

(Continued)

FOREIGN PATENT DOCUMENTS

JP   S5255428 A   5/1977
JP   H1176152 A   3/1999
(Continued)

*Primary Examiner* — Michael J Carey
*Assistant Examiner* — Christen A. Sharpless
(74) *Attorney, Agent, or Firm* — N.V. Nederlandsch Octrooibureau (57) ABSTRACT

An endoscope includes a dichroic prism assembly configured to receive light from an object image through an entrance face. The assembly includes a first prism and a further dichroic prism assembly for splitting light in three light components, the first prism having a cross section with corners designed so that an incoming beam is partially reflected twice inside and exits the first prism through an exit face towards a first sensor. The dichroic prism assembly includes a compensator prism between the first prism and the further dichroic prism assembly. A first path length travelled by the part of the incoming beam reflected twice inside the first prism towards the first sensor is the same as path lengths travelled by a part of the incoming beam entering the further dichroic prism assembly towards each of three sensors, accounting for adjustment for focal plane focus position difference in wavelengths at the sensors.

13 Claims, 11 Drawing Sheets

(51) Int. Cl.
  *G02B 23/24* (2006.01)
  *G02B 27/10* (2006.01)
  *G02B 27/14* (2006.01)
(52) U.S. Cl.
  CPC ..... *G02B 23/2484* (2013.01); *G02B 27/1013* (2013.01); *G02B 27/141* (2013.01)

(56) References Cited

U.S. PATENT DOCUMENTS

| | | | |
|---|---|---|---|
| 6,396,627 | B1 | 5/2002 | Tachihara et al. |
| 9,173,554 | B2 | 11/2015 | Fengler et al. |
| 9,642,532 | B2 | 5/2017 | Fengler et al. |
| 2005/0141097 | A1 | 6/2005 | Ho |
| 2009/0323192 | A1* | 12/2009 | Towndrow ............ G02B 23/08 359/634 |
| 2012/0105594 | A1* | 5/2012 | You ...................... H04N 5/2254 348/E13.074 |
| 2013/0271587 | A1* | 10/2013 | Tsuyuki ................ A61B 1/051 348/71 |
| 2014/0111813 | A1 | 4/2014 | Hamar |
| 2014/0194686 | A1* | 7/2014 | Murayama ........... A61B 1/0002 600/109 |
| 2015/0148630 | A1 | 5/2015 | Meester |
| 2016/0022126 | A1 | 1/2016 | Ramesh |
| 2016/0213236 | A1 | 7/2016 | Hruska et al. |
| 2017/0340861 | A1* | 11/2017 | Wildes ............... A61B 18/1492 |
| 2019/0175301 | A1* | 6/2019 | Ishikawa .............. A61B 5/1127 |

FOREIGN PATENT DOCUMENTS

| | | |
|---|---|---|
| JP | 2002000560 A | 1/2002 |
| JP | 2003250759 A | 9/2003 |
| JP | 2005526525 A | 9/2005 |
| JP | 2014524290 A | 9/2014 |
| JP | 2016077400 A | 5/2016 |
| JP | 2016178995 A | 10/2016 |
| JP | 2016181790 A | 10/2016 |

* cited by examiner

ENDOSCOPE COMPRISING A DICHROIC PRISM ASSEMBLY WITH AT LEAST FOUR CHANNELS

FIELD OF THE INVENTION

The present invention relates to a dichroic prism assembly, in particular a dichroic prism assembly with four or five channels. The dichroic prism assembly may be used in an endoscope tip.

BACKGROUND ART

Figure 1:
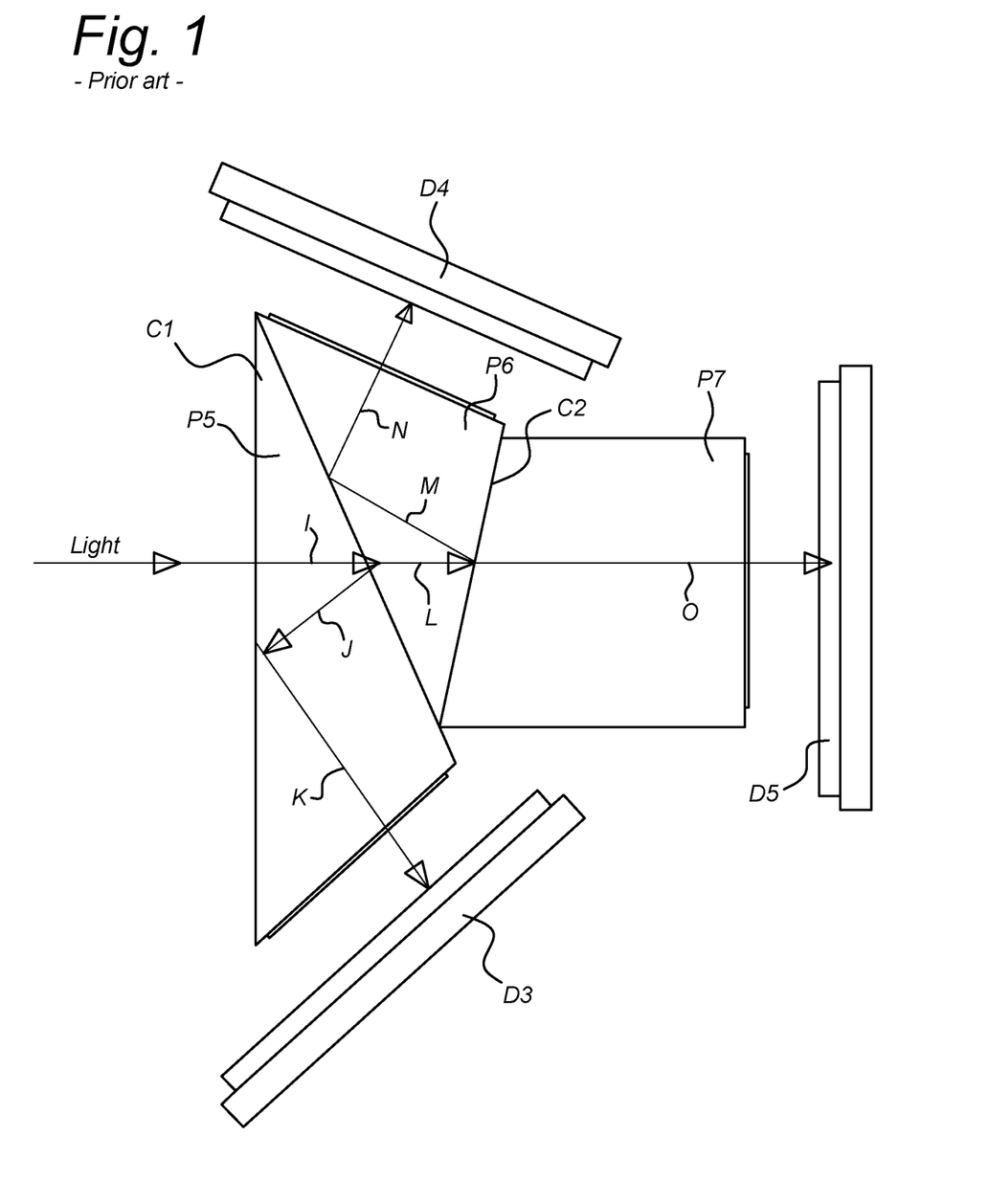
FIG. 1 schematically shows a dichroic prism assembly.

FIG. 1 shows a prism assembly comprising prisms P5, P6, and P7 for splitting light in red, green and blue components towards respective sensors D3, D4, and D5. The light enters the prism assembly through arrow indicated in FIG. 1. Between P5 and P6, an optical coating C1 is placed and between prisms P6 and P7 an optical coating C2 is placed, each optical coating C1 and C2 having a different reflectance and wavelength sensitivity. At C1, the incoming beam I is partially reflected back to the same face of the prism as through which the light entered (beam J). At that same face, the beam, now labelled K, is once again reflected towards sensor D3. The reflection from J to K is an internal reflection. Thus, sensor D3 receives light reflected by coating C1, and in analogue fashion sensor D4 receives light from beam L reflected by coating C2 (beams M and N), and sensor D5 receives light from beam O that has traversed the prism unhindered.

The system of FIG. 1 can only measure three light components (e.g. red, blue, green or alternatively RGB bayer, NIR, NIR) simultaneously. If more components (for example in the near infrared) are to be measured simultaneously, then the current state of the art is to use beam splitters to split off the channel of interest to the side and let the rest pass through. However, this increasing "stacking" of prisms and beam splitters has a problem that in order to have all sensors in its focal plane, the first prism is physically the largest, decreasing when progressing, in order to compensate the total focal length and compensate all sensors. Furthermore, due to mechanical constraints, these prisms are usually rotated 90 degrees along the incoming light axis, such that the prisms are not directly underneath P6 and P7, but rotated by 90 degrees, in which case they can be designed somewhat smaller.

Another drawback of the stacking of prisms is that each of these stacked prism elements relies on total internal reflection, requiring an airgap between each of the assembled prism elements in order to function correctly. From basic physics it follows that this cannot be solved by a e.g. a mirror coating without air gap. These air gaps need an outside construction to provide structural integrity of the optical system which is critical. Differences in temperature and component material expansion coefficients of these structural components need to be matched in order to avoid optical path alignment issues.

Another main issue with these setups is that in all cases, the sensors are opposite of each other adding to the structural electronical complexity with long cables and signal integrity. It is a problem that systems with more than three channels have a large size and system complexity due to these constraints.

U.S. Pat. No. 9,173,554 uses a dichroic prism assembly as outlined in FIG. 1. In order to be able to measure a fourth component for infrared fluorescence radiation, the optical path leading to sensor D3 is used to detect both red (R) and infrared (IR) light, in time alternating fashion. This approach has a number of drawbacks. First of all, in the time domain the resolution is halved due to the required switching. This makes real-time applications less attractive and motion artefacts at the halved video rates will be introduced. It also does not allow for any calculations that require simultaneous multiple signals from different wavelengths. Second, the red and infrared images cannot both be exactly in focus. Due to a large wavelength difference between red and infrared, at best either the IR image is sharp and in focus or the R image is sharp and in focus.

Due to the switching, the sensors can only be set at the same exposure time, because switching exposure time would require sensor settings that influence with the readout timing and exposure time, which can no longer overlap and finally influence either framerate and/or sensitivity of the system as well as adding a great deal of system processing complexity. Finally, gain needs to be switched heavily to differ between low signal-strength IR signals and relatively high signal-strength R signals. This negatively influences either the sensitivity of the IR channel and/or the red channel as well as frame time due to time it takes to apply the sensor settings before starting the exposure.

It is an object of the invention to provide a practical solution which does not require time-switching of the received signals.

SUMMARY OF THE INVENTION

The invention provides an endoscope comprising a dichroic prism assembly according to claim 1.

In an embodiment of the invention, a different approach is used compared to the state of the art. Instead of splitting the incoming beam outwards, that is, away from the incoming beam, it is split inward, that is, the light path crosses its own incoming beam. By having the split-off beam cross the incoming beam, the path length is increased substantially, compared to the outward splitting as used in e.g. FIG. 1. By using this inward splitting, the overall prism size can be reduced while still allowing path length matching between all optical paths. Unlike the state of the art of FIG. 1, where an internal reflection is used from beam J to beam K, in prism P1 a non-internal reflection B to C is used.

In an embodiment of the invention, the second IR prism is enclosed with 2 wedge shaped prisms which can move up/down and have at least one sloped side, such that moving up/down will increase and/or decrease the path length. When increasing the path length before the 4th prisms to compensate channel 4 to match channel 5, the other wedge prism behind channel 4 can be used to decrease and/or increase the stage behind the 4th channel.

Furthermore the invention allows for placing both sensors of the IR channels at the same time of the object, allowing for a small mechanical construction, as opposed to standard stacking elements which usually have sensors on opposite sides of the prisms, or are spaced apart far, creating a big system. By not using internal reflections at these first two stages, no large external construction is required to facilitate in creating the airgaps required for internal reflection. This allows for an easy and stable (both mechanically as optically) construction without external components, which saves complexity, space, weight and as such adds to the overall structure stability.

In an example, a medical imaging system is provided comprising at least one dichroic prism assembly as described above, wherein at least two infrared imaging wavelength (e.g. between 640 and 1000 nm) sensors and three visible wavelength (e.g. red, green, and blue) sensors are used, wherein each of the sensors are optically pixel to pixel aligned with a accuracy of better than ⅓th of a pixel. The imaging system may be used for real-time applications during surgery. In an embodiment, the frame rate is at least 60 frames per second (fps) and the pixels are sampled with at least 8 bits.

In an embodiment, the two infrared wavelengths are in the 700-800 nm range for methylene blue and in the 800-900 nm range for ICG, respectively.

The invention is defined by the appended claims. All embodiments not falling under the scope of the appended claims are to be considered merely as examples suitable for understanding the invention.

BRIEF DESCRIPTION OF THE DRAWINGS

The present invention will be discussed in more detail below, with reference to the attached drawings, in which.

DESCRIPTION OF EMBODIMENTS

Figure 2:
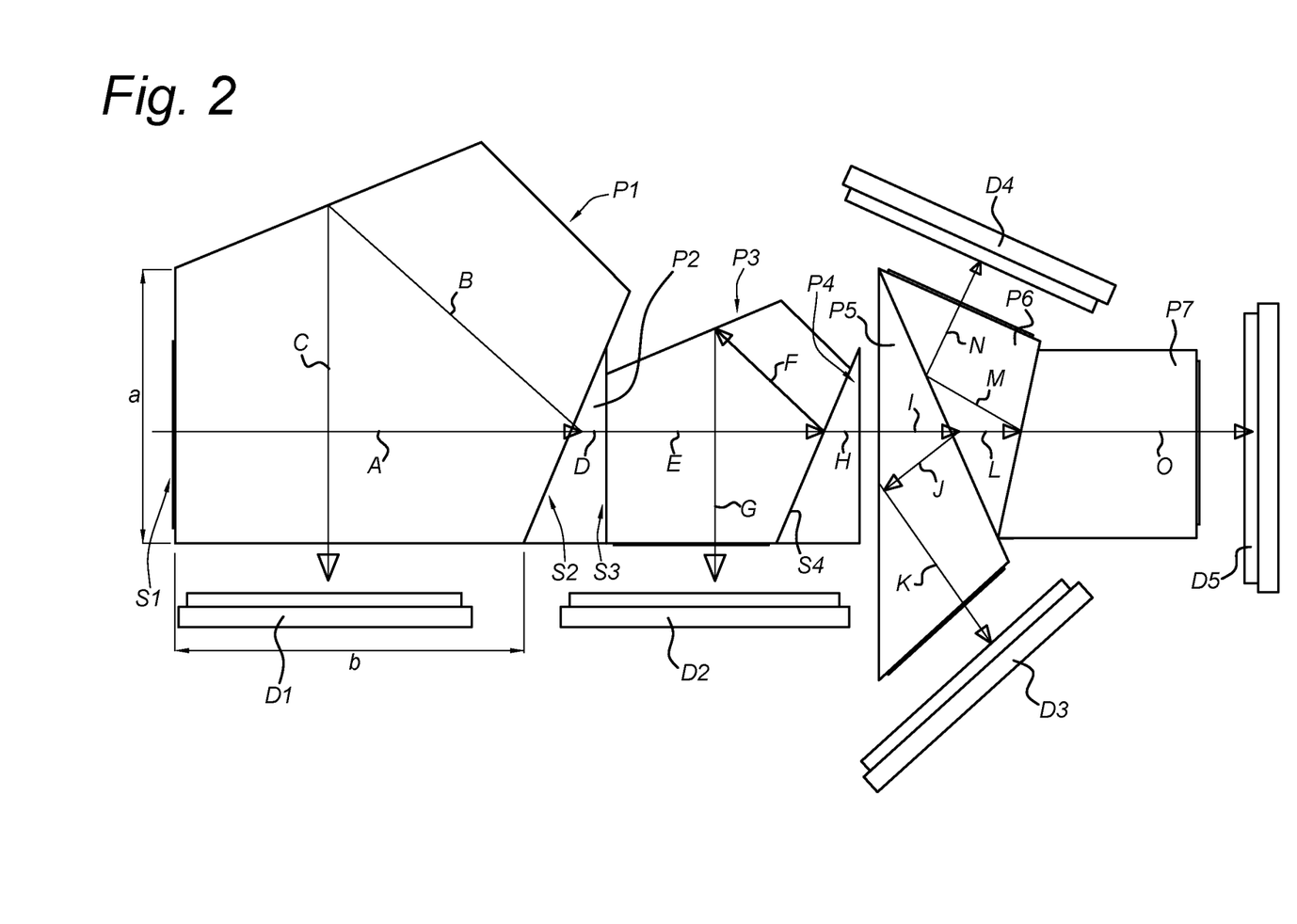
FIG. 2 schematically shows a dichroic prism assembly according to an embodiment of the invention.

FIG. 2 schematically shows a dichroic prism assembly according to an embodiment of the invention.

In an embodiment of the invention, a first pentagonal prism P1 is used. In an embodiment, the incoming light beam A is partially reflected on face S2, being one of the two faces not adjoining the entrance face S1. The reflected beam B is then reflected against a first one of the faces adjoining the entrance face. The angle of reflection can be below the critical angle, so that the reflection is not internal (in an embodiment, the adjoining face is coated to avoid leaking of light and reflect the required wavelength of interest). The reflected beam C then crosses itself (beam A) and exits the prism through the second one of the faces adjoining the entrance face, towards sensor D1. A part of the beam A goes through face S2 and enters compensating prism P2.

In an embodiment according the invention, prism P1 does not use internal reflection to reflect the incoming beam towards sensor D1. In an embodiment, two non-internal reflections are used to direct the incoming beam A via beams B and C towards sensor D1. In an embodiment there are no airgaps between prisms P1 and P2. In an embodiment, there are no airgaps between prisms P3 and P4. In an embodiment, there are no airgaps between prisms P2 and P3.

Prism P2 is a compensator prism which will be described in more detail in reference to FIGS. 5*a-d*.

In an embodiment of the invention, from P2 the beam D enters a second pentagonal prism P3. As in prism P1, inward reflection is used to make the beam cross itself. For brevity, the description of the beam will not be repeated, except to state that in prism P3, the beam parts E, F, and G correspond to beam parts A, B, and C in prism P1, respectively.

In an embodiment according the invention, prism P3 also does not use internal reflection to reflect the incoming beam towards sensor D2. In an embodiment, two non-internal reflections are used to direct the incoming beam E via beams F and G towards sensor D2. In an embodiment there are no airgaps between prisms P1, P2, P3, and P4.

After prism P3, there is another compensating prism P4. Finally, beam H enters the dichroic prism assembly comprising prisms P5, P6, and P7, with sensors D3, D4, and D5 respectively. The dichroic prism assembly of P5, P6, and P7 has already been described in reference to FIG. 1. In an embodiment, between prism P4 and prism P5 there is an air gap.

In FIG. 2, the following total path lengths are defined for each endpoint channel (defined in terms of the sensor at the end of the channel):

Sensor D1 (e.g. first near infrared) path: A+B+C
Sensor D2 (e.g. second near infrared) path: A+D+E+F+G
Sensor D3 (e.g. red) path: A+D+E+H+I+J+K
Sensor D4 (e.g. green) path: A+D+E+H+I+L+M+N
Sensor D5 (e.g. blue) path: A+D+E+H+I+L+O In an embodiment, the path lengths are matched, so that A+B+C=A+D+E+F+G=A+D+E+H+I+J+K=A+D+E+H+I+L+O=A+D+E+H+I+L+M+N. The matching of path lengths can comprise an adjustment for focal plane focus position differences in wavelengths to be detected at the sensors D1-D5. That is, for example the path length towards the sensor for blue (B) light may not be exactly the same as the path length towards the sensor for red (R) light, since the ideal distances for creating a sharp, focused image are somewhat dependent on the wavelength of the light. The prisms can be configured to allow for these dependencies.

The D+H lengths can be adjusted and act as focus compensators due to wavelength shifts, as will be described in reference to FIG. 5*a-d*.

A larger airgap in path I can be used for additional filters or filled with glass compensator for focus shifts and compensation. An airgap needs to exist in that particular bottom surface of red prism because of the internal reflection in the path from beam J to beam K. A space can be reserved between the prism output faces and each of the sensors D1-5 to provide an additional filter, or should be filled up with glass compensators accordingly.

An advantage of the fact that P1 and P3 use essentially the same reflection paths, is that this way the optical assembly can have sensors mostly on one side (D1, D2, D3 are all on one side), still use an even amount of direction change so all sensors see the same image and no mirror effects need to be compensated for.

Normally optical prisms are designed as in the case of the three channel blue and red channels, and that way the path length would require a very long prism, which would result in a large module which is less suitable for use in an endoscope or handheld imaging system. Furthermore the two channels (sensors D1 and D2) would need to be opposite of each other which also makes the electronics more cumbersome as the large distance between the 2 sensors. In the embodiment of FIG. 2, the two sensors D1 and D2 can be on the same side as prisms P1 and P3.

According an embodiment of the invention, the first two prisms P1, P3 have a pentagonal shape where at least five corners are used and all corners have an inside angle >=90 degree.

Each of these prisms has an additional compensator prism P2, P4 to create a flat exit surface pane for the light and at the same time have a path length compensation function to be able to match the path lengths of all sensors.

In an embodiment according to the invention, the dimensions are given as follows. Total height of the module is ≤30 mm or smaller for a 5-channel configuration including the sensors. The maximum width ≤15 mm. The maximum length ≤45 mm.

In an embodiment according the invention, a system using a dichroic prism assembly has a capability to create image resolutions in full color without artifacts at 3840×2160 @ 12 bit per color at 60 Fps without using infrared frame insertion. Infrared frames are available as well at these same resolution @ 12 bit.

Another advantage of the current invention is that because all surfaces that connect the paths to D1 and D2 are flat. Accordingly the modules (P1, P2, P3, P4) can be easily aligned which makes automatic assembly easy. These modules can be prepared individually and afterwards bonded together with a simple robotic or manual tool.

The second prism P3 (for the D2 path) can be smaller than the prism P1 (for the D1 path), because path length A is already compensated for. In order to shape the first prism for the path to D1 with a slightly longer length (A) a perfect match can be created between the total internal path to D1 and compensate as much as possible for the total length of the path to D2.

The pentagonal prisms are usually not regular. For example, length a (influencing the length of beams B and C) of the P1 cross section may be smaller than length b (influencing the length of beams A and B).

Figure 3:
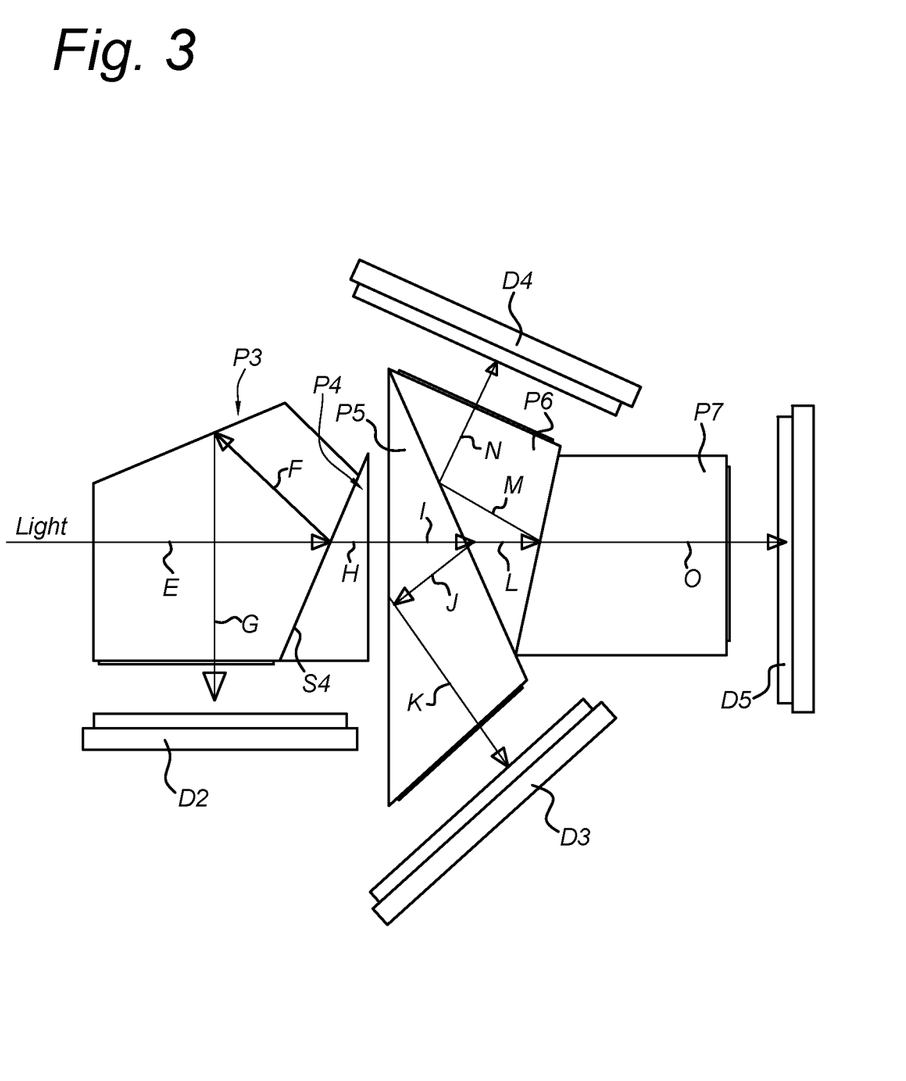
FIG. 3 schematically shows a further dichroic prism assembly according to an embodiment of the invention.

FIG. 3 schematically shows a dichroic prism assembly according to an embodiment of the invention. Compared to FIG. 2, the first pentagonal prism P1 and the first compensator prism P2 are absent. The resulting dichroic prism assembly of FIG. 3 has four channels, each respective channel formed by a path to one of the sensors D2-D5. The following path lengths are defined for each channel:

Sensor D2 (e.g. near infrared) path: E+F+G
Sensor D3 (e.g. red) path: E+H+I+J+K
Sensor D4 (e.g. green) path: E+H+I+L+M+N
Sensor D5 (e.g. blue) path: E+H+I+L+O The path lengths are matched, so that E+F+G=E+H+I+J+K=E+H+I+L+O=E+H+I+L+M+N.

Figure 4A:
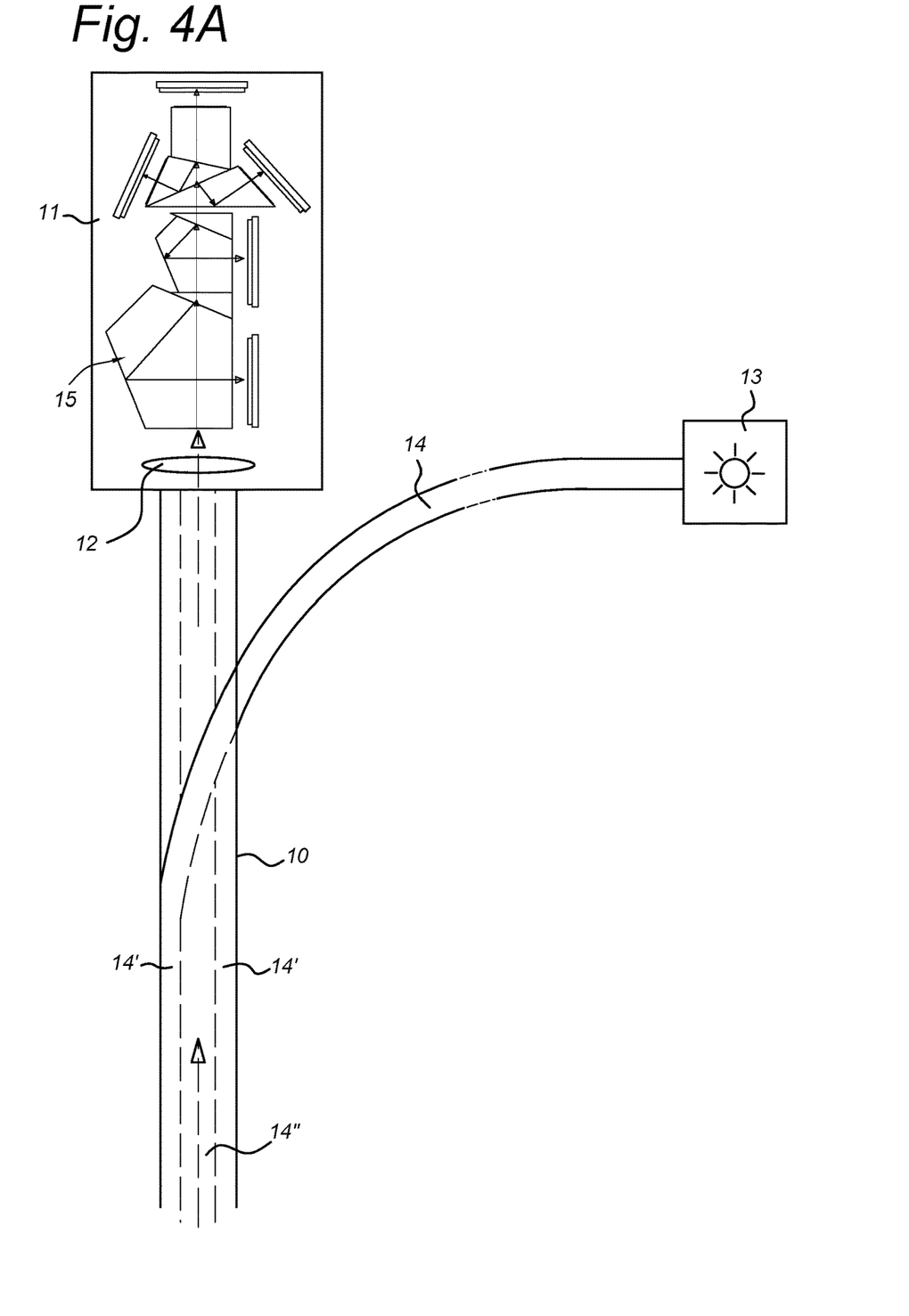
FIGS. 4*a-c* schematically show an endoscope and cabling according to an embodiment of the invention.

FIG. 4a schematically shows an endoscope 10 or laparoscope 10, according to an embodiment of the invention. For the purposes of this invention, the differences between laparoscopes and endoscopes are relatively small, so where the description mentions an endoscope, a laparoscope configuration is usually also possible. The endoscope/laparoscope 10 comprises camera module 11 including a dichroic prism assembly 15 such as shown in FIG. 2 or 3. The camera module 11 may also include an additional lens 12 for focusing incident light onto the entrance face of the dichroic prism assembly 15. This last lens 12 may also be integrated in the last part of the endoscope part to match the prism back focal length. An optical fiber 14 connected to a light source 13 couples light into the endoscope 10. Inside the endoscope, optical fiber 14 splits off into several fibers 14'.

Inside the laparoscope a lens system is created consisting of lens elements and/or relay rod lenses (similar as in standard laparoscopes) or, in an endoscope configuration, a fiber bundle can be used like in a standard flexible endoscope. Furthermore a processing unit (not shown) may be placed in the camera module 11 for high speed image processing and image cleanup to optionally reduce data such that it does not have to be transmitted.

In another embodiment of the invention, the processing unit is placed further away from the imaging system and optical elements. A key issue with specifically endoscopy systems, but also open configurations, is the cabling which provides the electronic signals of the systems to be transferred between the processing unit and the image sensors placed on the prism elements, and the cables that provide the lighting to the object that is imaged. Most configurations have 2 cabling systems based on Low Voltage Differential Signals (LVDS). The data transfer speed of these cables however is mostly limited to the length of the cable. The optical configuration proposed in this invention means that more data needs to be transferred at a higher bitrate than usual in endoscopic medical imaging systems. Usability and size are largely hindered by the fact that two cables are required (one for light and one electrical for the image and control signals). Simply adding more cable pairs is the standard solution, but the downside of this is that the minimal required thickness of the cables is limiting the flexibility and agility of the camera head. Furthermore the cables will become thicker in diameter and heavier and more electronics is required inside the camera head, which makes the camera head larger and heavier.

Figure 4B:
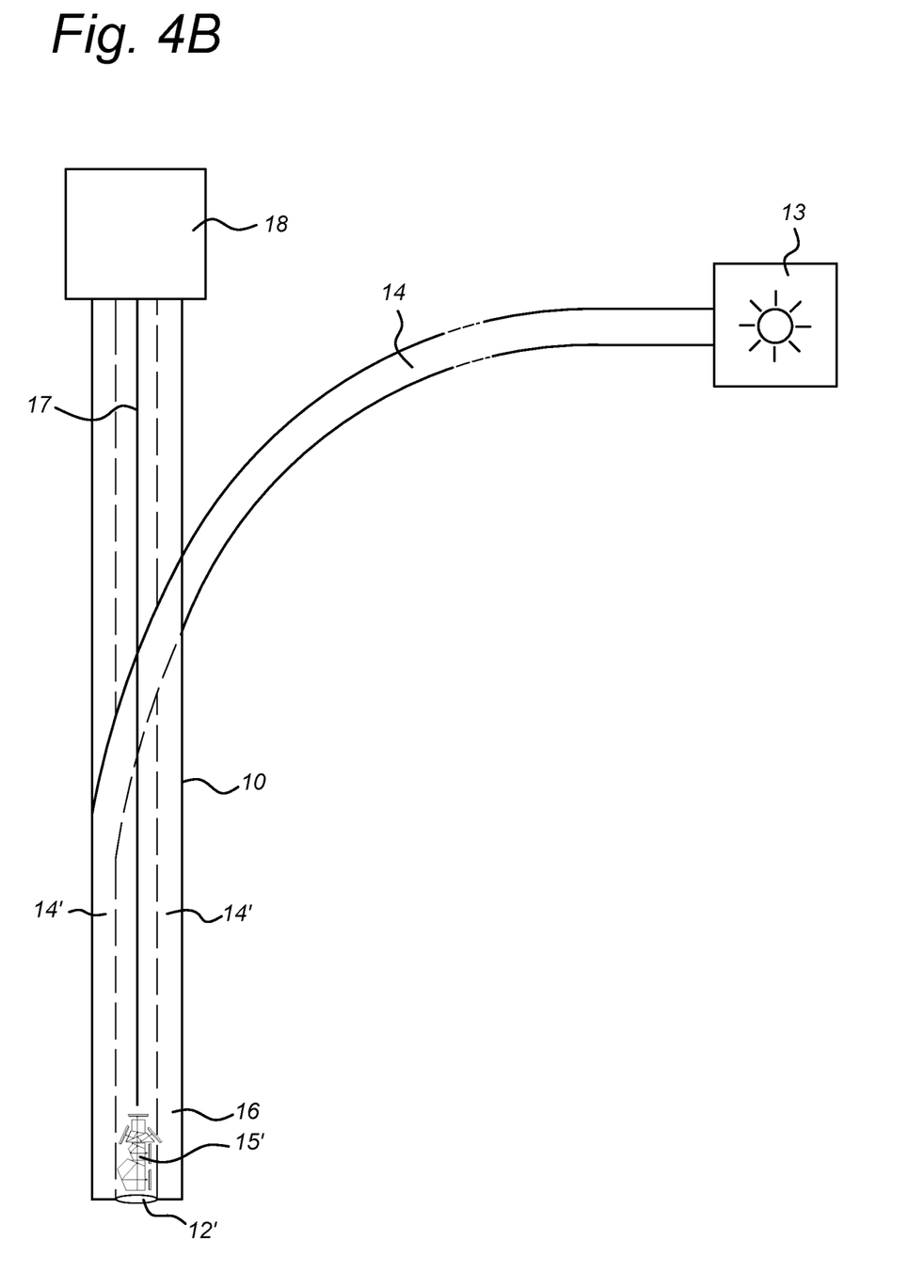

FIG. 4b shows an embodiment where the dichroic prism assembly 15' (for example the assembly shown in FIG. 2 or 3) and the lens 12' are located in the tip (e.g.: distal end, or distal part) of endoscope 10. In this embodiment, there is no need to transport light from the tip to the camera module. However, it is necessary now to transport the signal from the sensors D1-D5 to the module 18 housing the processing unit. The rod relaying lenses normally placed in the tube of the laparoscope, or the fibers in case of an endoscope are no longer required, and only a simple lens system 12' needs to be placed in front of the prism assembly.

Figure 4C:
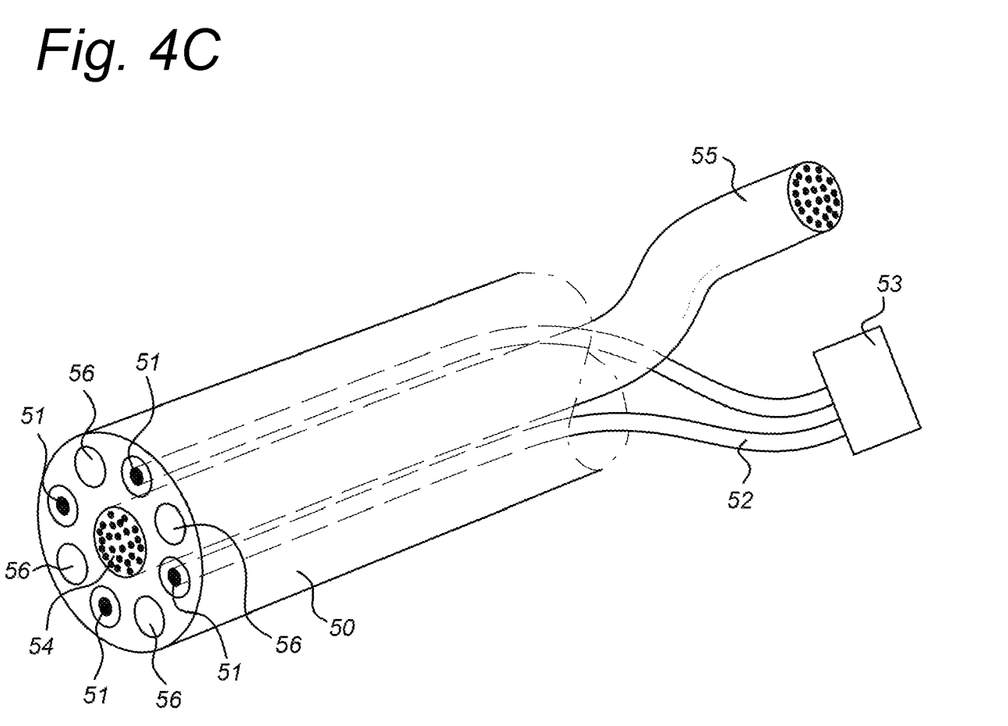

In any of these embodiments, it is possible to include four small diameter coax cables 51 and place these around/integrate these with the fiber optic cable 54. The cable is then fused, together with optional filler cables 56 to improve stability, as an integrated part and a single cable, which is directly coupled between camera and control system with light engine. Such an arrangement is shown in FIG. 4c, where central core fiber 54 can carry light from the light engine to the tip of the endoscope, and the diameter coax cables 51 can carry the signal from detectors D1-D5 located in the tip to the processing unit in housing 53. Depending on the amount of data to be transferred and the required length of the coax cables 51, a suitable number of coax cables can be selected, e.g. one, two, three, four, or more.

Figure 5A:
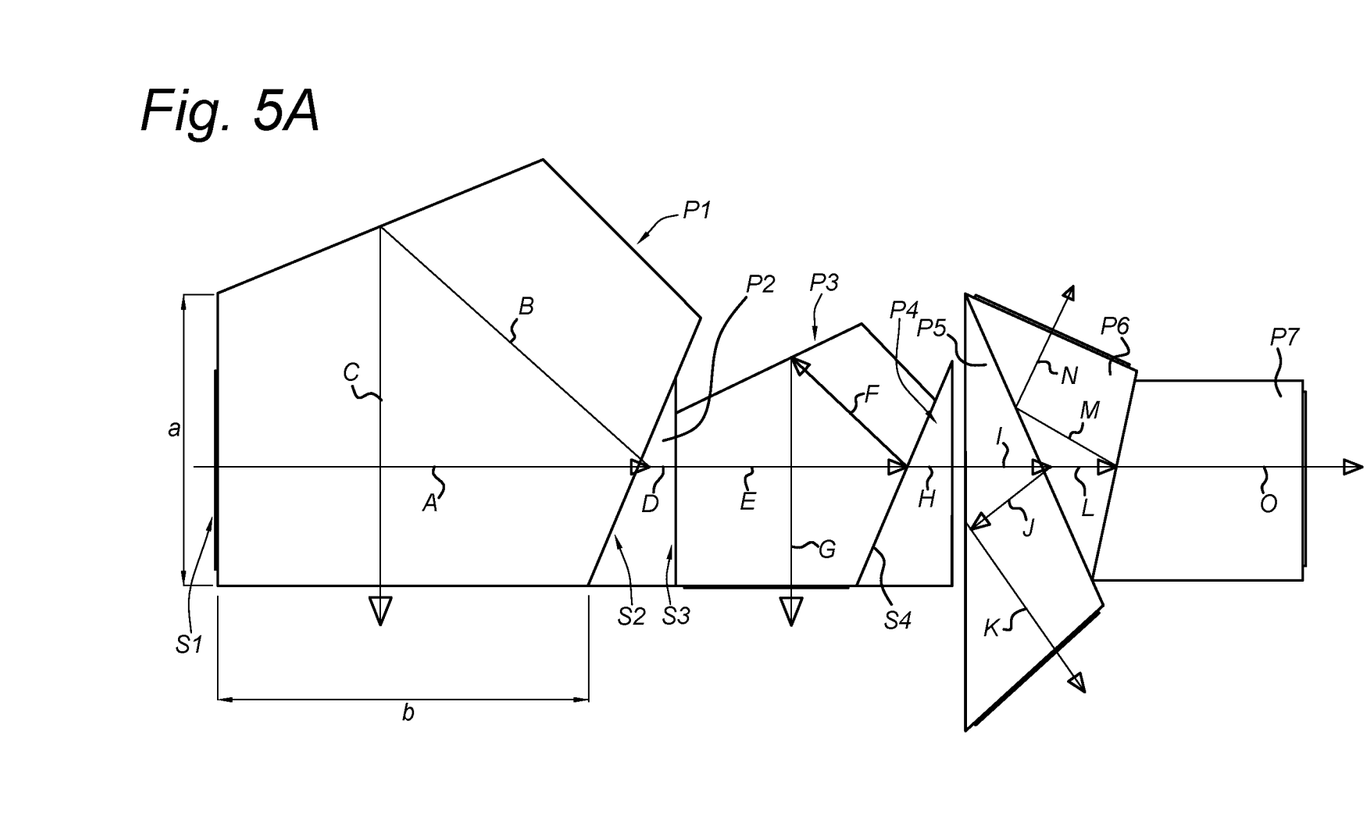
FIGS. 5*a-d* schematically show dichroic prism assemblies with movable compensator prisms according to an embodiment of the invention.

FIGS. 5a-d schematically show dichroic prism assemblies with movable compensator prisms according to an embodiment of the invention. FIG. 5a shows the same configuration as FIG. 2, with optical axis of prisms P1, P2, P3, and P4 aligned (which in this example coincides with the bottoms of all prisms being aligned).

Figure 5B:
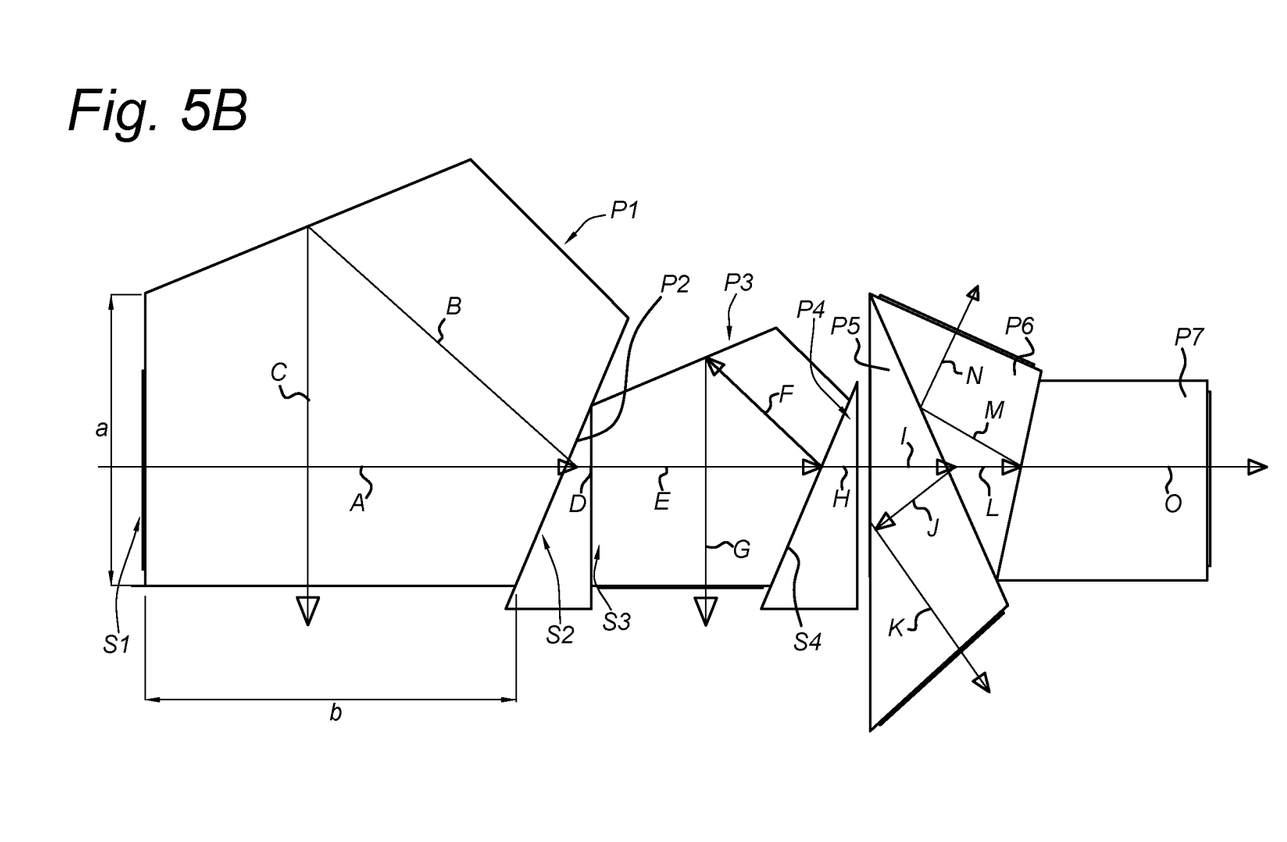

FIG. 5b shows prisms P2 and P4 shifted downwards compared to prisms P1, P3 and P5-P7 which are still in the same vertical position as in FIG. 5a. The prisms P3 and P5-P7 have been shifted to the left so that the prisms still connect with downward shifted compensator prisms P2 and P4 (it is also possible to move P1 to the right). There is still no airgap between P1 and P2 or between P3 and P4. As a result, the path lengths D and H in FIG. 5b are slightly shorter than the original path lengths D and H in FIG. 5a. In other words, each of the paths to sensors D2, D3, D4, D5 is now a little shorter compared to the path to sensor D1. Moreover, the paths to sensors D3, D4 and D5 is now a little shorter compared to the path to sensor D2 as well. If prisms P2 and P4, were moved in the opposite direction (upwards in FIG. 5b), the paths to D2, D3, D4, D5 would be a little longer compared to the path to sensor D1. In all cases the optical axis of prisms shall remain the same. Additionally prisms P1 and P3 may be moved up/down slightly to change the position along the optical axis of the imaging sensor (left/right) to perfectly match the best achieved mechanical position. This would furthermore have an impact on the total path length of each of the sensors and hence, according an embodiment of the invention the two compensator prisms P2 and P4 are movable to correct for this change in path length.

Figure 5C:
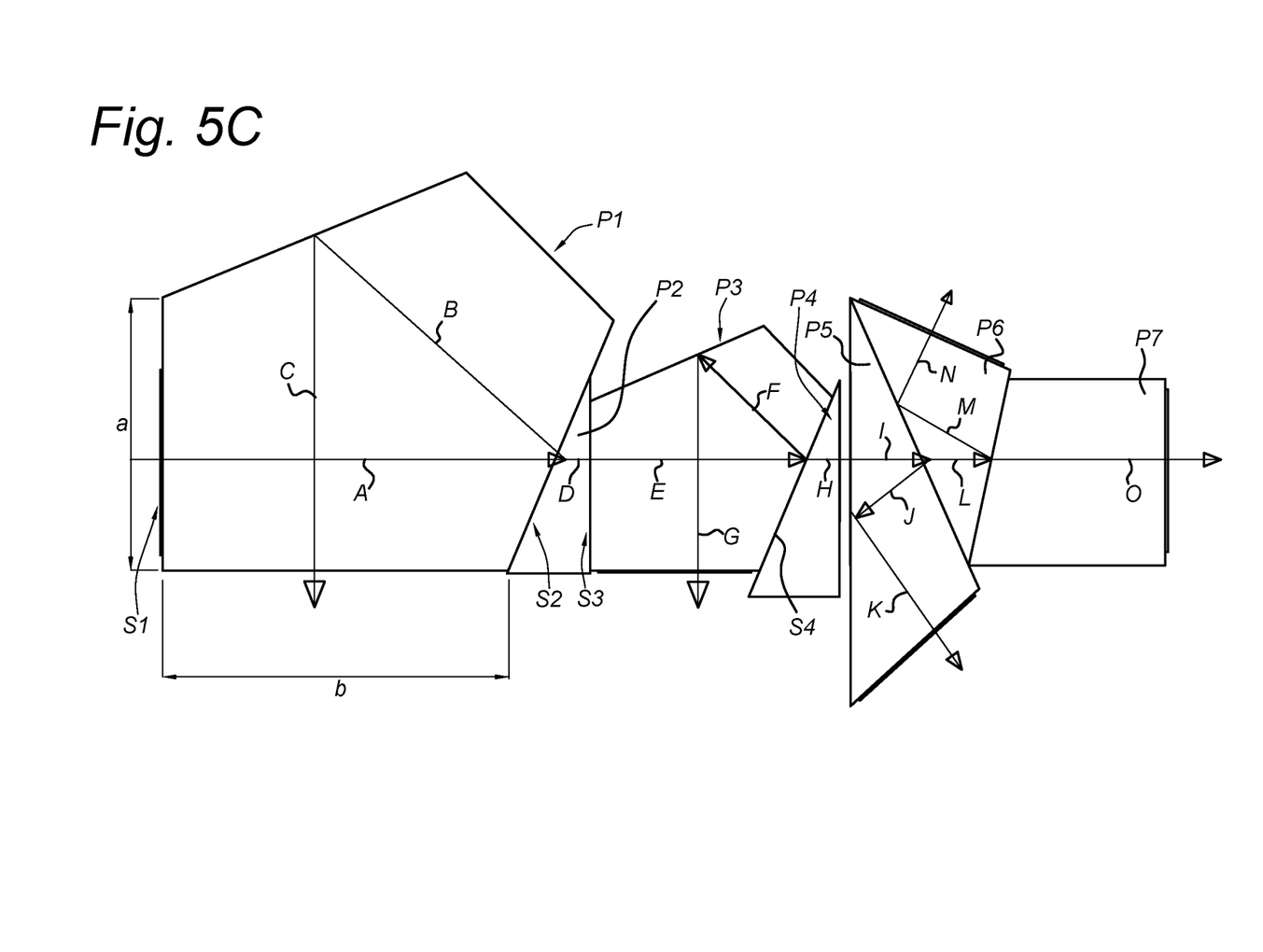

In FIG. 5c, prism P4 is shifted with respect to P1-P3 and P5-P7. The paths to sensors D3, D4, D5 is slightly decreased compared to the path to sensors D1 and D2. The prisms P5-P7 remain on the same optical axis.

Figure 5D:
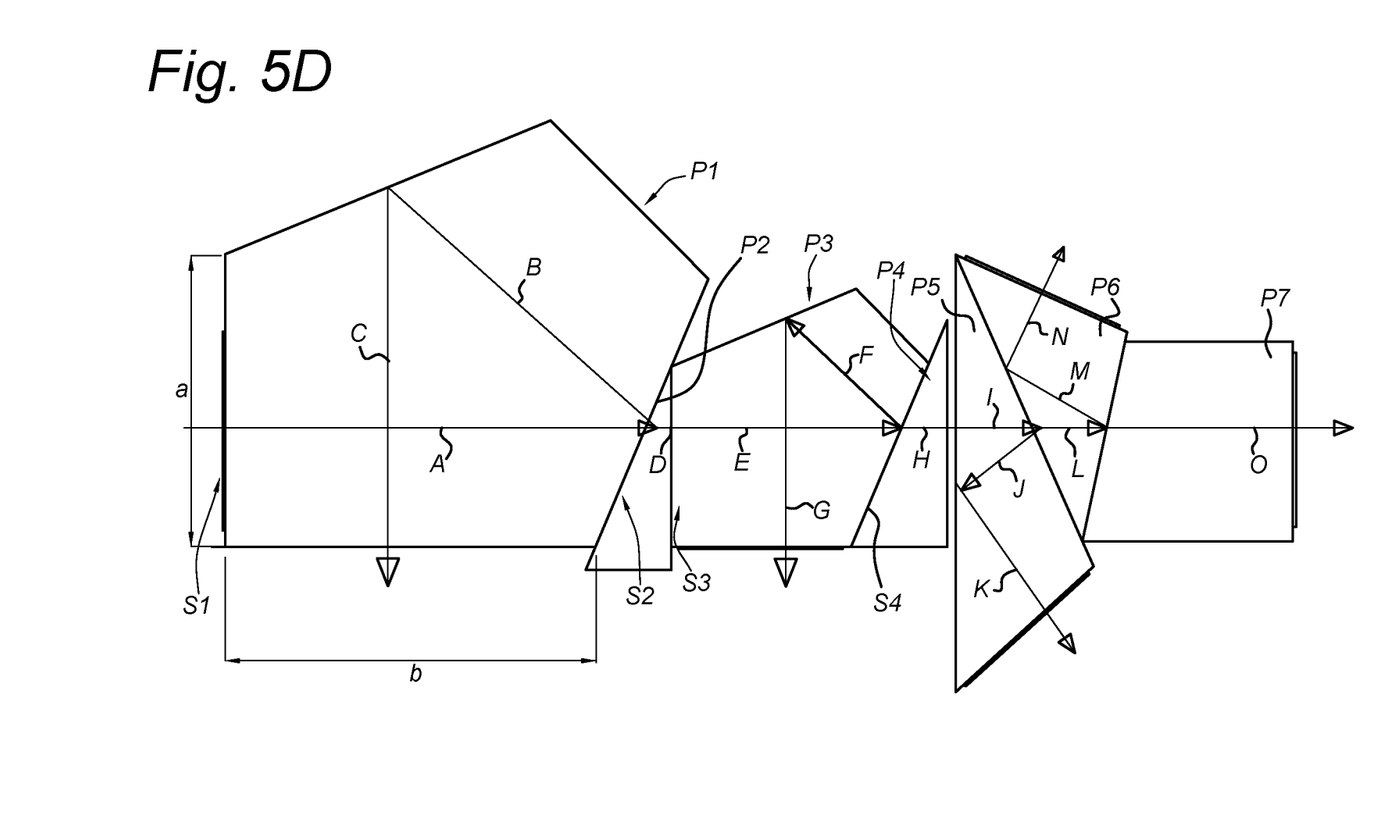

In FIG. 5d, the prism P2 is shifted downwards which result in P3-P7 to also move slightly to the left, so that prisms P1 and P2 are still connected to each other without air gap as well as P3 and P4. The paths to sensors D2-D5 is slightly decreased compared to the path to sensors D1.

FIGS. 5a-d show a few example path length adjustments that can be made by shifting compensator prisms P2 and/or P4 while maintaining a connection without air gap with prisms P1 and P3. Other adjustments are possible as well. The key point is that by adjusting the compensator prisms, small adjustments can be made so that the path lengths towards all five sensors match, e.g. depending on the wavelengths used in each of the sensors D1-D5.

In embodiments according the invention, the optical axis of the prisms P1, P3, and P5-P7 remains the same, in other words, these prisms are not moved in a vertical direction. This is practical, because by only moving P2 and P4 in a vertical direction, only the path lengths D and H are affected, while the others A-C, E-G, I-O remain the same. Moving e.g. P1 in a vertical direction would also affect path lengths A, B, and C, making the effect of the vertical adjustments harder to understand. However, the invention does not exclude embodiments in which any one or more of the prisms P1, P3, P5-P7 are moved vertically in order to adjust path lengths.

Figure 6A:
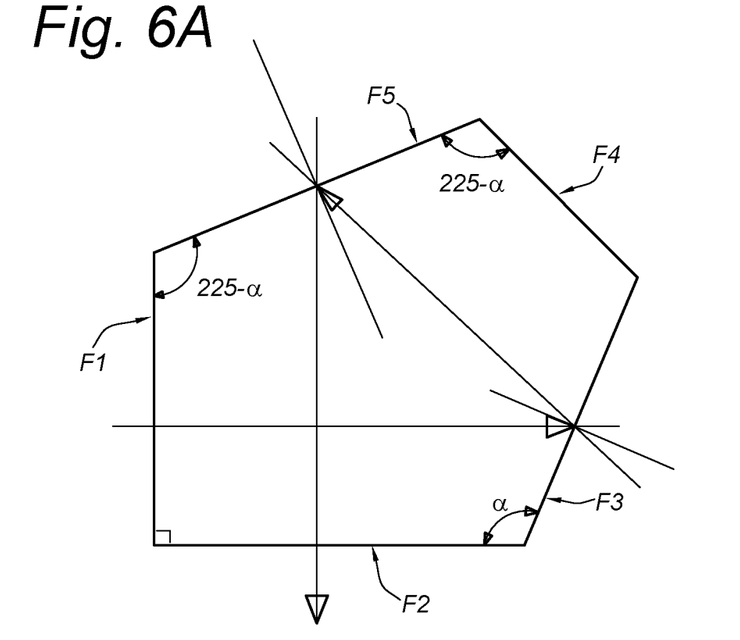
FIGS. 6*a-b* shows an exemplary pentagonal prism for use in an dichroic prism assembly according to an embodiment of the invention.

FIG. 6a shows a cross section of an exemplary pentagonal prism for use in a dichroic prism assembly according to an embodiment of the invention.

In an embodiment, the prism P1 or P3 has corners which are designed so that an incoming beam which enters the entrance face in a direction parallel to a normal of said entrance face is reflected twice inside the prism and exits the prism through an exit face parallel to a normal of said exit face, wherein the normal of the entrance face and the normal of the exit face are perpendicular to each other.

A skilled person can design such a prism. In the example of FIG. 6a, one of the five angles is a right angle (between faces F1 and F2), two angles have a first value $\alpha \geq 90$ degrees (between faces F2 and F3 and F3 and F4) and two angles have a second value $225-\alpha$ degrees (between faces F1 and F5 and F5 and F4), making a total inside angle of 540 degrees for a pentagonal prism. As can be easily verified, the pentagonal prism as shown in FIG. 6a will inwardly reflect an incoming horizontal beam, incoming through face F1 in parallel with the normal of face F1, using two reflections against faces F3 and F5, so that it exits the prism in a vertical direction through face F2, in parallel with the normal of face F2. In the first reflection, at face F3, the beams will make an angle with the normal of the face of reflection of $\alpha-90$ degrees. In the second reflection, at face F5, the angle with the normal of the face of reflection is $135-\alpha$. In this example, the angle $\alpha$ should have a value $90<\alpha<135$.

In a specific embodiment, the value of a is 112.5 degrees, so that the pentagonal prism has one right angle and four angles of 112.5 degrees.

Figure 6B:
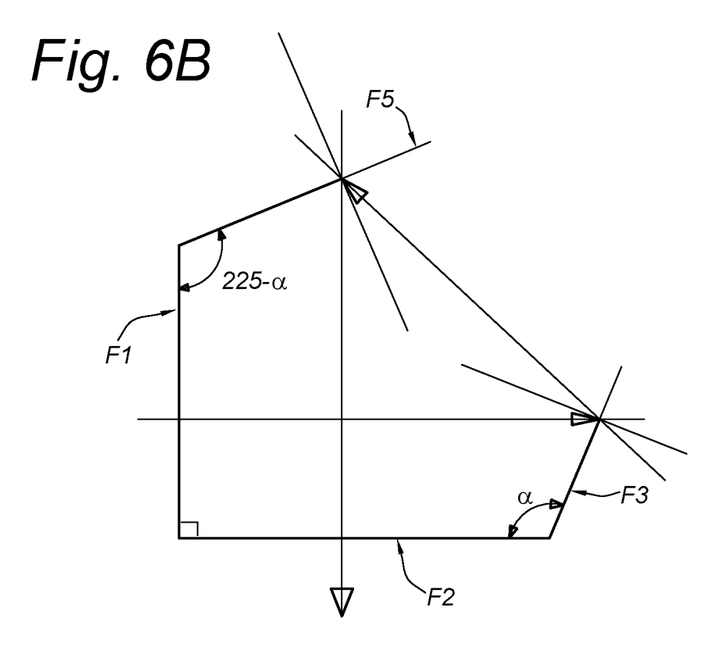

FIG. 6b shows a reduced part of the prism of FIG. 6a. As can be seen from the construction of the lines, it is sufficient if one angle in the prism is 90 degrees (between F1 and F2), an angle adjoining the 90 degrees angle is $\alpha$, and the other angle (between F1 and F5) adjoining the 90 degrees angle is $225-\alpha$. The angles between F3 and F4 and F4 and F5 can in fact be freely chosen.

The skilled person will also be able to design prisms in which the incoming and outgoing beams are not at right angles to each other. However, there are practical advantages to designs, such as the embodiment of FIG. 6b, wherein the incoming and outgoing chief ray beam are at a right angle to each other, as additional angles of light are coming from the lens system.

A pentagonal prism shape is a logical and practical choice for the prisms P1 and P3. However, as is clear from FIG. 6b, in order to create the conditions for the required reflections, in fact many different types of prism shape will serve. The invention is therefore not limited to the use of pentagonal prisms.

In the foregoing description of the figures, the invention has been described with reference to specific embodiments thereof. It will, however, be evident that various modifications and changes may be made thereto without departing from the scope of the invention as summarized in the attached claims.

In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims.

In particular, combinations of specific features of various aspects of the invention may be made. An aspect of the invention may be further advantageously enhanced by adding a feature that was described in relation to another aspect of the invention.

It is to be understood that the invention is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

Features of the present invention will be further understood by the following clauses: Clause 1. A dichroic prism assembly (P1-P7) configured to receive light from an object image through an entrance face of the dichroic prism assembly, comprising a first prism (P3) and a further dichroic prism assembly (P5, P6, P7) for splitting light in three light components, the first prism having a cross section with at least five corners, each corner having an inside angle of at least 90 degrees, wherein the corners of the first prism are designed so that an incoming beam which enters the entrance face in a direction parallel to a normal of said entrance face is reflected twice inside the prism and exits the prism through an exit face parallel to a normal of said exit face, wherein the normal of the entrance face and the normal of the exit face are perpendicular to each other, and wherein the dichroic prism assembly comprises a compensator prism (P4) between the first prism and the further dichroic prism assembly.

Clause 2. The dichroic prism assembly (P1-P7) according to clause 1, wherein the prism is a pentagonal prism.

Clause 3. The dichroic prism assembly (P1-P7) according to clause 2, wherein the pentagonal prism has one right angle, two angles α and two angles 225−a, wherein 90<α<135.

Clause 4. The dichroic prism assembly (P1-P7) according to any of the previous clauses, wherein the first prism (P3) and the compensator prism (P4) have their optical axes aligned, and the compensation prism is movable with respect to the first prism (P3) in a direction parallel to a normal of the optical axis while maintaining a connection to the first prism.

Clause 5. A dichroic prism assembly (P1-P7) according to any of the preceding clauses, comprising a second prism (P1), the second prism having a cross section with at least five corners with an inside angle of at least 90 degrees.

Clause 6. The dichroic prism assembly (P1-P7) according to clause 5, wherein a first side of the first prism (P3) is provided with a first sensor (D2) and a second side of the second prism (P1) is provided with a second sensor (D1).

Clause 7. The dichroic prism assembly (P1-P7) according to clause 6, wherein the first sensor (D2) and/or the second sensor (D1) is an infrared light sensor.

Clause 8. The dichroic prism assembly (P1-P7) according to clause 6 or 7, wherein, when light enters the second prism (P1) through a first surface (S1), the light will be partially reflected towards the second sensor (D1), thereby travelling a first path length, and the light will partially enter the first prism (P3) and be partially reflected towards the first sensor (D2), thereby travelling a second path length, wherein the second prism is larger than the first prism so that the first and the second path lengths are the same.

Clause 9. The dichroic prism assembly (P1-P7) according to any one of the previous clauses 6-8, comprising a further compensator prism (P2) connected to the second prism (P1).

Clause 10. The dichroic prism assembly (P1-P7) according to any one of the previous clauses, wherein each prism in the further dichroic prism assembly (P5, P6, P7) is provided with a sensor (D3, D4, D5).

Clause 11. Endoscope or laparoscope (10) comprising at least one dichroic prism assembly (15) according to any one of the previous clauses.

Clause 12. Endoscope or laparoscope (10) according to clause 11, further comprising a lens (12) for focusing light onto the dichroic prism assembly.

Clause 13. A medical imaging system comprising at least one dichroic prism assembly (15) according to clause 10 wherein at least two infrared imaging wavelength sensors (D1, D2) and three visible light wavelength sensors (D3, D4, D5) are used, wherein each of the sensors are optically pixel to pixel aligned with a accuracy of better than ⅓th of a pixel.

Clause 14. The endoscope or the laparoscope according to clause 11 or 12 or the medical imaging system of clause 13, using an integrated cable comprising an optical fiber core (54) for providing light from a light engine onto a surgical field to illuminate, the optical fiber core surrounded by a plurality of coax cables (51) for transporting sensor data.

Clause 15. The endoscope or the laparoscope according to clause 11 or 12 when dependent on clause 10 or the medical imaging system according to clause 13, wherein the two infrared wavelength sensors operate in the 700-800 nm range and in the 800-900 nm range, respectively.

Clause 16 The endoscope or the laparoscope according to clause 11, 12, or 14 or the imaging system according to clauses 13 or 14, wherein a frame acquisition frequency is at least 60 frames per second and a sampling rate is at least 8 bits per pixel.

FIGURE REFERENCES

P1: First pentagonal prism
P2: First compensator prism
P3: Second pentagonal prism
P4: Second compensator prism
D1: First sensor
D2: Second sensor
P5: dichroic prism of further dichroic prism assembly
P6: dichroic prism of further dichroic prism assembly
P7: dichroic prism of further dichroic prism assembly
D3: red light sensor
D4: blue light sensor
D5: green light sensor
A-O: path segments
10: endoscope/laparoscope/medical imaging system
11: camera module
12: lens
13: light source
14: optic fiber
15: dichroic prism assembly
51: coax cable
52: coax cable cover
53: housing
54: fiber optic cable
55: fiber optic cable cover
56: filler cable.

The invention claimed is:

1. An endoscope comprising, in a distal part, a dichroic prism assembly (P1-P7) configured to receive light from an object image through an entrance face of the dichroic prism assembly, the dichroic prism assembly comprising a first prism (P3) and a further dichroic prism assembly (P5, P6, P7) for splitting light in three light components, the first prism having a cross section with at least five corners, each corner having an inside angle of at least 90 degrees,
    wherein the corners of the first prism are designed so that an incoming beam which enters the entrance face in a direction parallel to a normal of said entrance face is partially reflected twice inside the first prism and exits the first prism through an exit face parallel to a normal of said exit face towards a first sensor (D2),
    wherein the normal of the entrance face and the normal of the exit face are perpendicular to each other, and
wherein the dichroic prism assembly comprises a compensator prism (P4) between the first prism and the further dichroic prism assembly,
    wherein a first path length travelled by the part of the incoming beam reflected twice inside the first prism towards the first sensor (D2) is the same as a second path length travelled by a part of the incoming beam not reflected inside the first prism and entering the further dichroic prism assembly (P5, P6, P7) towards one of three sensors (D3, D4, D5), taking into account an adjustment for focal plane focus position difference in wavelengths to be detected at the first sensor and the three sensors, wherein the first path length is measured from the entrance face to the first sensor and wherein the second path length is measured from the entrance face to the one of three sensors.

2. The endoscope according to claim 1, wherein the first prism is a pentagonal prism.

3. The endoscope according to claim 2, wherein the pentagonal prism has one right angle, two angles α and two angles 225−α, wherein 90<α<135.

4. The endoscope according to claim 1, wherein the first prism (P3) and the compensator prism (P4) have their bottoms aligned.

5. The endoscope according to claim 1, wherein the dichroic prism assembly (P1-P7) comprises a second prism (P1), the second prism having a cross section with at least five corners with an inside angle of at least 90 degrees.

6. The endoscope according to claim 5, wherein a second side of the second prism (P1) is provided with a second sensor (D1).

7. The endoscope according to claim 6, wherein at least one of the first sensor (D2) and the second sensor (D1) is an infrared light sensor.

8. The endoscope according to claim 6, wherein, when light enters the second prism (P1) through an entrance face (S1) of the second prism (P1), the light is partially reflected towards the second sensor (D1), thereby travelling a first path length, and the light partially enters the first prism (P3) and is partially reflected towards the first sensor (D2), thereby travelling a second path length, wherein the second prism (P1) is larger than the first prism (P3) so that the first and the second path lengths are the same.

9. The endoscope according to claim 1, comprising a further compensator prism (P2) connected to the second prism (P1).

10. The endoscope according to claim 1, further comprising a lens for focusing light onto the dichroic prism assembly.

11. The endoscope according to claim 1, using an integrated cable comprising an optical fiber core for providing light from a light engine onto a surgical field to illuminate, the optical fiber core surrounded by a plurality of coax cables for transporting sensor data.

12. The endoscope according to claim 6, wherein the first sensor (D2) and the second sensor (D1) are infrared light sensors, and operate in the 700-800 nm range and in the 800-900 nm range, respectively.

13. The endoscope according to claim 1, wherein a frame acquisition frequency is at least 60 frames per second and a sampling rate is at least 8 bits per pixel.

* * * * *